US008202273B2

(12) United States Patent
Karidis

(10) Patent No.: US 8,202,273 B2
(45) Date of Patent: Jun. 19, 2012

(54) ORTHOPEDIC FIXATION DEVICE WITH ZERO BACKLASH AND ADJUSTABLE COMPLIANCE, AND PROCESS FOR ADJUSTING SAME

(76) Inventor: John Peter Karidis, Ossining, NY (US)

( * ) Notice: Subject to any disclaimer, the term of this patent is extended or adjusted under 35 U.S.C. 154(b) by 1087 days.

(21) Appl. No.: 12/110,563

(22) Filed: Apr. 28, 2008

(65) Prior Publication Data

US 2008/0269741 A1 Oct. 30, 2008

Related U.S. Application Data

(60) Provisional application No. 60/926,597, filed on Apr. 28, 2007.

(51) Int. Cl.
*A61B 17/00* (2006.01)
(52) U.S. Cl. ........................................... 606/56
(58) Field of Classification Search ............... 606/56, 606/54, 57, 58, 59, 90
See application file for complete search history.

(56) References Cited

U.S. PATENT DOCUMENTS

| 4,536,114 | A | 8/1985 | Belew |
| 5,601,551 | A | 2/1997 | Taylor et al. |
| 5,702,389 | A | 12/1997 | Taylor et al. |
| 5,891,143 | A | 4/1999 | Taylor et al. |
| 5,919,192 | A * | 7/1999 | Shouts ............................ 606/56 |
| 6,030,386 | A | 2/2000 | Taylor et al. |
| 6,383,156 | B1 | 5/2002 | Enzerink et al. |
| 6,537,275 | B2 | 3/2003 | Venturini et al. |
| 2002/0010465 | A1 | 1/2002 | Koo et al. |

FOREIGN PATENT DOCUMENTS

WO WO03086212 10/2003

OTHER PUBLICATIONS

International Search Report and the Written Opinion of the International Searching Authority, International Application No. PCT/US2008/061756, dated Sep. 19, 2008.
International Search Report and the Written Opinion of the International Searching Authority, International Application No. PCT/US2008/071604, dated Feb. 4, 2009.
International Search Report and the Written Opinion of the International Searching Authority, International Application No. PCT/US2008/071671, dated Feb. 19, 2009.

(Continued)

*Primary Examiner* — Eduardo C Robert
*Assistant Examiner* — James Palmer
(74) *Attorney, Agent, or Firm* — Myers Wolin, LLC

(57) ABSTRACT

An orthopedic fixator for positioning a first element relative to a second element with precision and with controlled compliance which can be adjusted during the healing process. One embodiment comprises a first frame for attachment to the first element, a second frame attached to the first frame through a plurality of adjustable effective length struts, and a third frame for attachment to the second element, wherein the third frame is compliantly attached to the second frame. A preferred embodiment comprises adjustable length preload elements to apply unidirectional forces between the first and second frames so as preload the adjustable effective length struts and substantially reduce the positional tolerance. An alternative embodiment comprises adjustable spring elements allowing the compliance of the attachment of the third frame to the second frame to be adjusted at various points in the healing process.

20 Claims, 13 Drawing Sheets

OTHER PUBLICATIONS

URL: http://global.smith-nephew.com/us/TAYLOR_SPATIAL_FRAME_7441.html Retrieved: Mar. 10, 2009.

URL: http://global.smith-nephew.com/us/ILIZAROV_EXTERNAL_FXR_OVW_13957.html Retrieved Mar. 10, 2009.

URL: http://www.orthofix.com/products/sheffield.asp Retrieved Mar. 10, 2009.

URL: http://global.smith-nephew.com/us/JET_X_BAR_UNILATERAL_FIX_7243.html Retrieved Mar. 10, 2009.

URL: http://www.orthofix.com/products/xcaliber_fixator2.asp Retrieved Mar. 10, 2009.

URL: http://www.jcharlestaylor.com/spat/01Correction.html Retrieved Mar. 10, 2009.

* cited by examiner

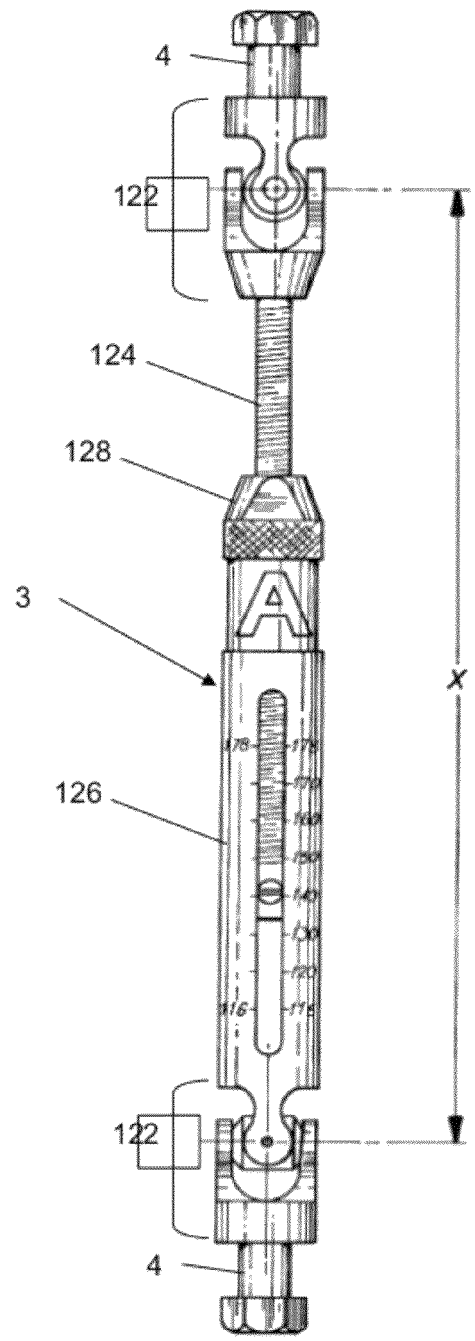
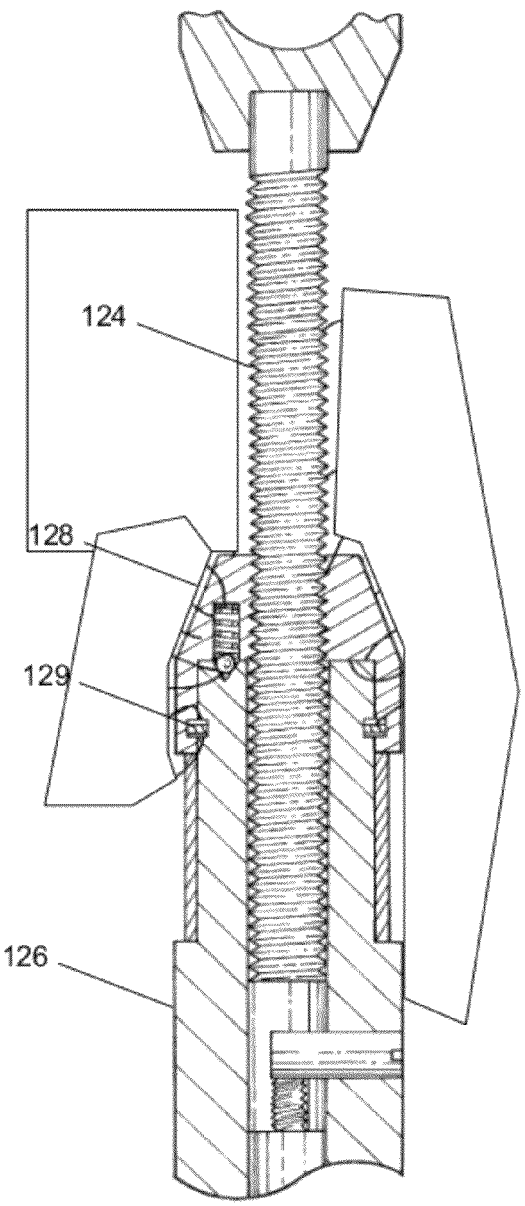
Fig. 2A
Prior Art
Fig. 2B
Prior Art

ORTHOPEDIC FIXATION DEVICE WITH ZERO BACKLASH AND ADJUSTABLE COMPLIANCE, AND PROCESS FOR ADJUSTING SAME

CROSS REFERENCE TO RELATED APPLICATIONS

This application claims the benefit of U.S. Application 60/926,597, filed Apr. 28, 2007, the contents of which are incorporated herein by reference.

FIELD OF THE INVENTION

This invention relates generally to orthopedic fixation systems and more specifically to an improved external fixator with zero backlash and continuously adjustable compliance, and process for adjusting same.

BACKGROUND

For centuries, external splints of various forms have been used to provide skeletal support to injured or healing limbs. For decades, various forms of external fixation have been used by orthopedic surgeons to support bones that are healing from traumatic fracture, or that are healing from reconstruction surgery intended to correct deformities by repositioning, lengthening or shortening various bone segments. These external fixation devices can use single shafts attached to bone elements by half-pins, or circular arcs or rings which can be attached to bone elements by half-pins or by tensioned wires that pass all the way through the limb (known as the Ilizarov technique).

In general, the goal of these external fixators is to maintain the relative position of two bone segments during healing. The desired relative position may be fixed (as in the case of simple trauma healing) or variable (as in the case of gradual bone lengthening or deformity correction). Also, the desired stiffness of the system may be very high in some cases, such as the initial healing phase of unstable oblique fractures, and may be lower in other cases where some external load sharing by the healing bone is desired. Many types of external fixators have been developed. One of the most sophisticated, adaptable, and easily adjustable of these is the Taylor Spatial Frame, developed by Harold S. Taylor, J. Charles Taylor, et al, and marketed by Smith & Nephew, Inc.

Taylor et al., U.S. Pat. No. 5,702,389 describes a variety of fixator types, and discloses a ring-type external fixator based on a six-degree-of-freedom "Stewart Platform." In this design, six adjustable-length struts are used to connect a first base member for mounting to a first bone element to a second base member for mounting to a second bone element. Spherical joints which are common to the ends of two different struts are used to pivotably mount the struts to the base members.

Taylor et al., U.S. Pat. No. 6,030,386 retains the same basic structure of six adjustable-length struts connected between two base members, but replaces the spherical end joints with a combination of a rotating joint plus two pivoting joints which all share a common axis so as to allow independent rotation of each strut about its axis, in addition to the required two axis of pivoting required at the mounting ends.

Taylor et al., U.S. Pat. No. 5,891,143 discloses a particular design for a family of base members having different diameters, whereby all of the family members contain a circumferential array of holes with fixed separation, and whose total number is divisible by three. These holes are designed to support mounting blocks holding half-pins, Ilizarov wires, or other hardware which is attached to the bone elements.

The Taylor Spatial Frame provides good range of motion and adjustability, but each of a large number of mechanical joints and threaded parts in each strut adds some inevitable amount of mechanical clearance. The sum of all of these small mechanical tolerances results in a non-negligible amount of mechanical "play" in the system. The possible variations in the precise positioning and the distance between the strut ends create kinematic uncertainty that substantially limits the positional accuracy and precision by which the base members are held.

More specifically, the design of the Taylor Spatial Frame, as shipped commercially and as taught in U.S. Pat. No. 6,030,386, introduces small but necessary mechanical tolerances at several locations on each end of each adjustable length strut, including but not limited to radial and axial tolerances between the shoulder screw and the base member, radial and axial tolerances at each of the two pivot joints at each end, axial thread clearances between the threaded rod and the adjustment nut, and axial clearances between the internal retaining ring and the corresponding retential grooves in both the adjustment nut and non-threaded portion of the strut.

The end result of these cumulative tolerances is mechanical uncertainty (or "play") of somewhere on the order of 1 mm in any direction, and on the order of 1 degree in rotation about multiple axes. While some units may be substantially more accurate than this, the practical manufacturing tolerances that can be achieved on this many parts, together with the kinematic magnification of errors that can occur in some configurations, means that there may always be some perceptible level of clearance.

This mechanical clearance creates two deficiencies. The first deficiency is the inability of the structure to precisely and rigidly maintain the relative position of the base members. While the overall rigidity of the frame in high for large applied motions, the rigidity for small motions is nearly zero. This can result in unwanted bone motion and the unwanted transmission of external loads to the bones during certain healing phases. Furthermore, this mechanical clearance can result in the generation of acoustic noise in response to applied loads. The acoustic noise can potentially be noticeable enough to attract unwanted attention and/or to disturb the sleep.

An additional deficiency of the current art is the inability to controllably adjust the stiffness (or its inverse, the compliance) of the structure. The compliance of the external fixator determines the degree to which external loads are carried by the fixator frame itself, and the degree to which they are transmitted to and carried by the bone. Generally, it is believed that bone fracture healing and bone regeneration is affected by the level of mechanical rigidity that is provided by fixation devices during the healing process. Furthermore, it is generally believed that the optimal level of fixation rigidity varies during the fracture healing process, with maximum rigidity (i.e., minimum compliance) generally being most appropriate during the initial primary healing or callous formation phases, and with progressively lower rigidity (i.e., higher compliance) being most appropriate during the later callous remodeling phase when load sharing between the bone and the frame is required.

In summary, many current orthopedic fixation devices, such as the Taylor Spatial Frame, have manufacturing tolerances that significantly limit the maximum stiffness that can be achieved for small displacements, and no known available fixation devices provide a means for controllably adjusting the stiffness to a lower level (i.e., increasing the compliance of the fixator) if desired during later healing stages.

SUMMARY OF THE INVENTION

An orthopedic fixation device is provided that, in one embodiment, uses adjustable preloading elements to eliminate backlash and provide for more precise and stable fixation. Such device has several advantages including, but not limited to, reducing patient discomfort resulting from undesired motion and generating less mechanical noise. A further advantage is to provide a device whose stiffness can be adjusted to improve bone healing and patient comfort by providing a controllable level of load-sharing between the frame and the supported bones.

Yet another advantage is to provide a device having anisotropic stiffness so that axial motion has higher compliance than motion in other degrees-of-freedom. Still yet another advantage is to provide a device having the ability to adjust the anisotropic stiffness characteristics to provide a combination of linear motion and rotation in response to axial loading. Still yet another advantage of an embodiment of the invention is to provide an orthopedic fixation device having nonlinear force-deflection characteristics and motion limit-stops, to allow load sharing at low loads while limiting deflection at high loads.

In one embodiment of the invention, there is disclosed an orthopedic fixator for positioning a first element relative to a second element, said fixator comprising: a first frame for attachment to the first element, a second frame for attachment to the second element, a plurality of adjustable effective length struts connecting the first frame to the second frame so as to fix the position of the second frame relative to the first frame to within a positional tolerance, and means for applying unidirectional forces between the first and second frames so as preload the adjustable effective length struts and substantially reduce the positional tolerance.

In one embodiment, there is disclosed a process for adjusting the precise relative position of two elements connected by an orthopedic fixation assembly having a plurality of adjustable effective length struts having at least one adjustable preload element, comprising the steps of: substantially reducing the preload force generated by the preload element, adjusting the length of some or all of the adjustable effective length struts, and substantially increasing the preload force generated by the preload element to substantially reduce positional tolerances resulting from mechanical tolerances in the construction or assembly of the adjustable effective length struts or the orthopedic fixation assembly.

In accordance with an alternative embodiment of the invention, there is disclosed an orthopedic fixator for positioning a first element relative to a second element, said fixator comprising: a first frame for attachment to the first element, a second frame adjustably attached to the first frame, a third frame for attachment to the second element, and means for compliant attachment of the second frame to the third frame. Furthermore, the compliance of the attachment can be adjusted by changing the position of slidable clamp elements along the length of a portion of parallel spring plates. Additional aspects can include the use of cantilevered spring elements attached at both ends so as to provide non-linear force-deflection response, and mechanical limit-stops that prevent excessive motion of the bone elements even under high loading when the compliant structure is adjusted to provide low stiffness (i.e., high compliance).

In accordance with an alternative embodiment of the invention, there is disclosed an orthopedic fixator for positioning a first element relative to a second element, said fixator comprising: a first frame for attachment to the first element, a second frame adjustably attached to the first frame, a third frame for attachment to the second element, multiple adjustable compliant attachments of the second frame to the third frame, and means for independently adjusting the multiple adjustable compliant attachments to create an effective axis of maximum compliance the same as or different than the axis of maximum compliance of any of the individual compliant attachments.

In accordance with an alternative embodiment of the invention, there is disclosed an orthopedic fixator for positioning a first element relative to a second element, said fixator comprising: a first frame for attachment to the first element, a second frame, a third frame for attachment to the second element, a plurality of adjustable effective length struts connecting the first frame to the second frame so as to fix the position of the second frame relative to the first frame to within a positional tolerance, means for applying unidirectional forces between the first and second frames so as preload the adjustable effective length struts and substantially reduce the positional tolerance, and means for compliant attachment of the second frame to the third frame.

In accordance with an alternative embodiment of the invention, there is disclosed a process for orthopedic fixation of two skeletal elements during healing, comprising the steps of: fixing the position of a first skeletal element relative to a second skeletal element using an orthopedic fixator with adjustable compliance, adjusting the position and the compliance of the orthopedic fixator to minimize motion of the skeletal elements during a first phase of healing, increasing the adjustable compliance of the fixator in at least one preferred direction to a higher level during a second phase of healing, and optionally further increasing the compliance of the fixator in at least one preferred direction during subsequent phases of the healing.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

FIG. 2A is an elevational view of a prior art adjustable effective length strut.

FIG. 2B is a cross sectional view of a prior art adjustable effective length strut.

DETAILED DESCRIPTION OF THE PREFERRED EMBODIMENTS

Figure 1:
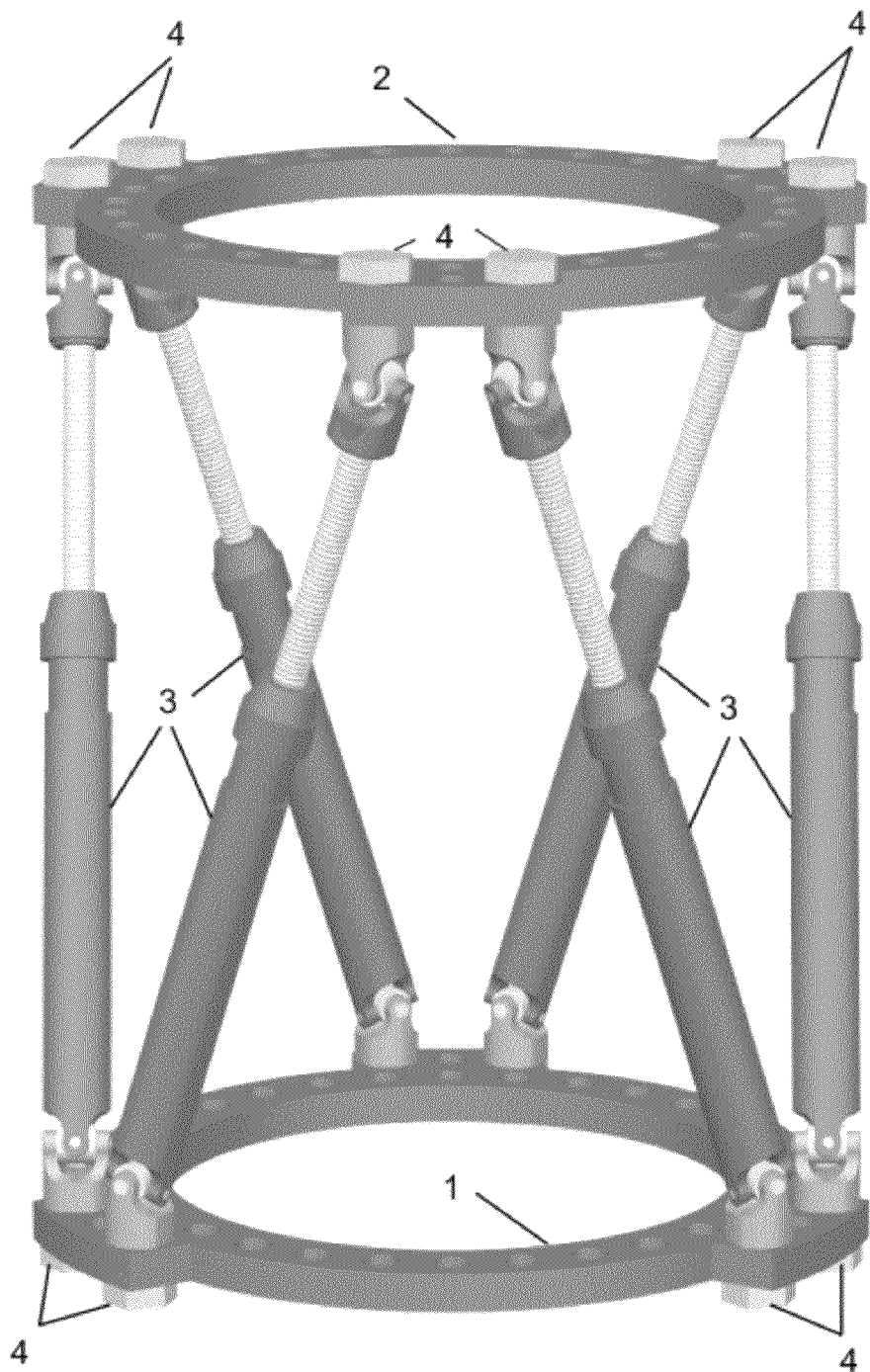
FIG. 1 is a perspective view of a prior art six-degree-of-freedom fixator device.

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner. In the various views of the drawings, like reference characters designate like or similar parts.

The improved orthopedic fixator device of the present invention benefits from two concepts that can be applied individually or in conjunction. The first concept focuses on the pre-loading of a fixator device to reduce backlash and is illustrated generally in connection with FIGS. 1-6. The second concept focuses on a benefit obtained through adjustable compliance and is illustrated generally in connection with FIGS. 7A-8B. The combination of such concepts is shown and described in connection with FIGS. 7A-12 that shows an improved fixator device subject to pre-loading and having adjustable compliance.

In addition, the improved orthopedic fixator device of the present invention is attached to human anatomy in a similar manner that is known in the art with other orthopedic fixator devices, and such attachment will therefore not be described herein in detail.

Pre-Loading

Turning first to FIG. 1, there is shown a six-degree-of-freedom external fixator known as the Taylor Spatial Frame, which is of the general type known as a "Stewart Platform". In this device, a lower frame 1 is provided to accept mounting features such as Ilizarov wires or half-pins which connect to a first bone element (not shown). There is also shown an upper frame 2, which similarly provides a mounting means for attachment to a second bone element (not shown). The relative position of the lower frame 1 and the upper frame 2 is determined by six adjustable effective length struts 3, which are generally rotatably attached to the lower frame 1 and upper frame 2 by a series of shoulder screws 4.

The adjustable effective length struts 3 are shown more clearly in FIG. 2A, where it can be seen that each strut 3 includes a dual-axis pivot or "universal joint" 122 at each end. The combination of the dual-axis pivot in the universal joint 122 and the rotating shoulder screw 4 creates a single effective pivot point for all three angular rotations. One of these universal joints 122 is mounted to a threaded rod 124, while the other universal joint 122 is mounted to the end of a cylinder 126, which surrounds at least part of the threaded rod 124. A rotating threaded collar 128 is threaded onto the rod 124, and is rotatably mounted to the end of the cylinder 126 using a retaining ring 129 as shown in the cross-sectional view of FIG. 2B. By rotating the threaded collar 128, the effective length "x" of the strut can be adjusted to any value between some minimum length and some maximum length. When adjusted to a given length, the adjustable effective length strut 3 will resist both forces trying to shorten it and forces trying to lengthen it. As a result, the position of upper frame 2, relative to the lower frame 1, can be approximately fixed in all six degrees of freedom (i.e., three translations and three rotations) by independently adjusting the lengths of the six struts 3 connecting upper frame 2 to lower frame 1.

While this structure provides a reasonably effective means of positioning frame 2 relative to frame 1, the accuracy and precision of this positioning is limited by several mechanical clearances and manufacturing tolerances associated with the parts of the strut 3 and its mounting to the frames 1 and 2 through the use of shoulder screws 4. More specifically, the exact effective length of each strut 3 can vary by an amount that depends on the following tolerances and clearances: vertical & lateral clearance between the shoulder screw 4 and the upper frame 2; clearance in the two pivots of the universal joint 122 near the upper frame 2; thread clearance between the thread rod 124 and the rotating threaded collar 128; axial play between the threaded collar 128 and the cylinder 126, as allowed by clearances around the retaining ring 129; clearance in the two pivots of the lower universal joint 122 near the lower frame 1; and vertical & lateral clearance between the shoulder screw 4 and the lower frame 1.

In general, mechanical clearances and tolerances between elements in a structure or mechanism can effectively be eliminated by applying forces to the elements which drive them to either the maximum or a minimum separation allowed by the tolerances or clearances. Thus, the imprecision caused by the clearances in the prior art fixator could be improved if all of the individual adjustable effective length struts 3, and their mounting to frames 1 and 2, can be preloaded either in tension or compression. The result would be the elimination of backlash, except in cases where some additional external loading exceeds the preload force and acts in the opposite direction. However, if individual actuators are preloaded, then six additional preload devices would be required. Fewer preload devices can potentially be used if each one can preload multiple actuators, but arbitrary positioning and orientation of the preload forces does not guarantee the preloading of all 6 degrees-of-freedom. Also, arbitrarily positioned preload devices, if rigid in some direction, can result in an over-constrained kinematic chain which will prevent the independent adjustment of the six primary actuators. Therefore, it is essential that any preload devices be positioned properly.

Figure 3:
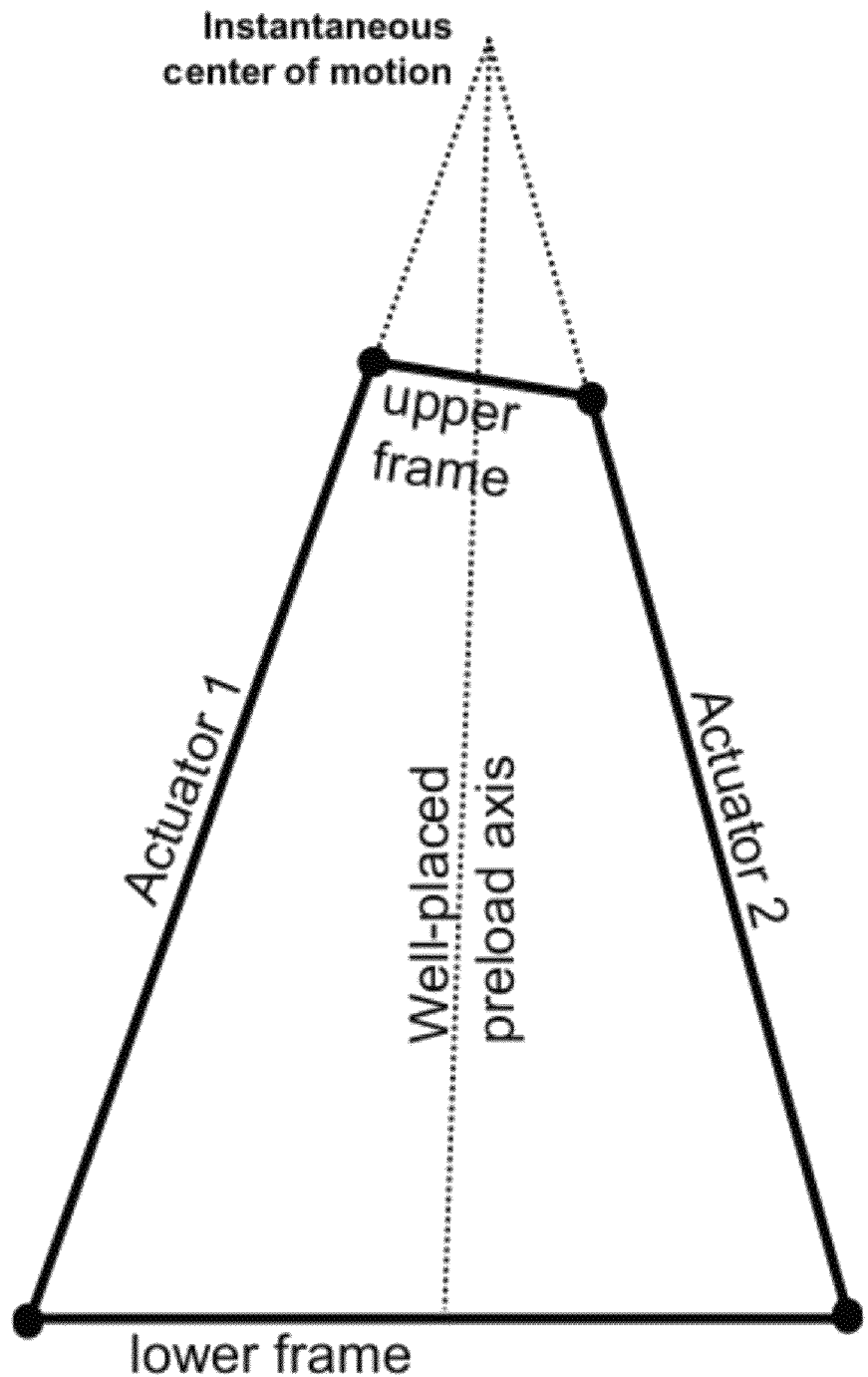
FIG. 3 is a schematic diagram illustrating a preloading operation used in an embodiment of a fixator device of the invention.

FIG. 3 schematically illustrates one very advantageous configuration where the preload forces act on the upper and lower frame at points which are approximately midway between the pivoting mounting points of two neighboring actuators. When so positioned, the combination of the preload device and the two preloaded actuators provides the same kinematic constraint as would two "perfect" zero-backlash actuators. The instantaneous center of motion (in the plane of the actuators) for a segment of the upper frame is at the intersection of the actuator axes. If a preload device also acts through this center of motion and also lies in the same plane as the actuators, then it can be pivotably attached to the upper and lower frames without adding to the kinematic constraints. Furthermore, if the preload axis approximately bisects the actuator axes, then the preload force will be evenly distributed across the two actuators. This example assumes the actuators and frame segments all lie in a common plane, but the same basic conclusion holds in three dimensions as well; a third link mounted at a fixed fraction of the distance between the end-points of the actuators on the upper and lower frames does not add a kinematic constraint, but can be used to preload the two actuators. In practice, it is not essential that the preload device be positioned exactly along the ideal axis.

Figure 4A:
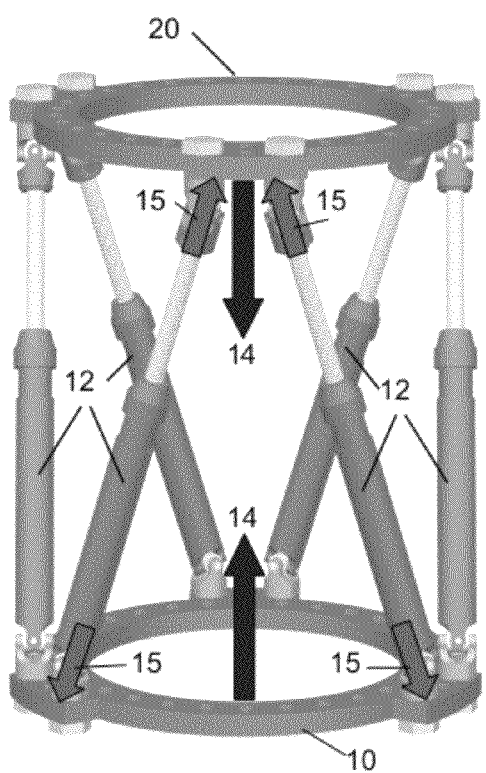
FIG. 4A is a schematic diagram illustrating use of a tensile element to provide compressive preloading of adjustable effective length struts used in an embodiment of the invention.

FIG. 4A schematically illustrates an embodiment of a fixator device of the invention and one way in which a single preload element can preload two adjustable length struts. Arrows 14 illustrate forces created by a single tension preload element, such as a spring or other elastic device, acting on a lower frame 10 and an upper frame 20 at points which are approximately midway between the mounting points where two adjustable struts 12 are mounted to the lower frame 10 and the upper frame 20. It will be appreciated to those skilled in the art that forces 14 created by a tension element will create compression forces, illustrated with arrows 15, within the neighboring adjustable length struts 12.

Figure 4B:
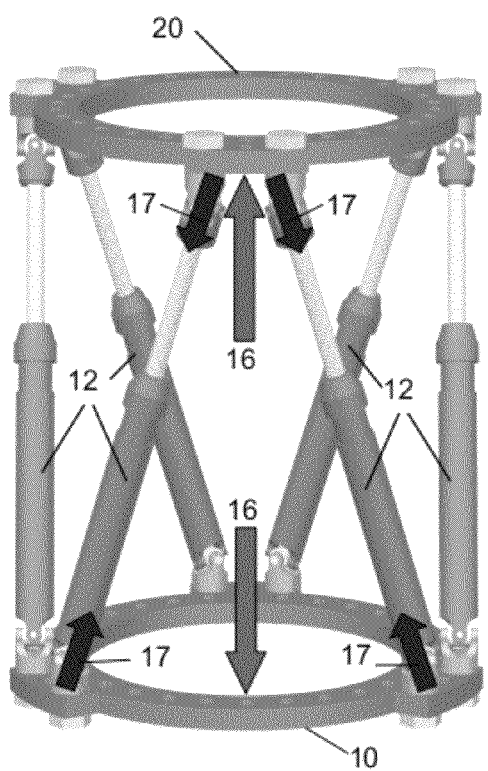
FIG. 4B is a schematic diagram illustrating use of a compressive element to provide tensile preloading of adjustable effective length struts used in an embodiment of the invention.

Conversely, FIG. 4B schematically illustrates a single preload element where preload forces indicated by arrows 16 are generated by a preload element that is under compressive loading. As before, these forces act on the lower frame 10 and the upper frame 20 at points which are approximately midway between the mounting points where two adjustable struts 12 are mounted to the lower frame 10 and the upper frame 20. It will again be appreciated to those skilled in the art that forces 16 created by a compressed preload element will create reaction tensile forces, illustrated by arrows 17, within the neighboring adjustable length struts 12.

While it might be considered that the preload forces could be generated using another adjustable length strut 12, such an approach would result in an over-constrained mechanism whereby the adjustment of the three struts will be coupled, thus preventing any large independent adjustment of any single strut and making overall frame adjustment very difficult. Another possible approach might be to use highly compliant spring elements to generate the preload forces. While this could work in principle, and while it could theoretically be used to create preload forces that never have to be adjusted when the frame is adjusted, such an approach introduces an additional risk. Specifically, if a highly stressed elastic element is used to create the preload forces, a structural failure (or intentional or accidental removal) of any one of the adjustable struts would result in a catastrophic failure where the high elastic preload element would generate very large displacements of the frame. Such displacements could be strong enough and large enough to cause significant injury, and therefore should be avoided if at all possible. What is needed, therefore, is a convenient means to generate preload forces which act only over a short distance, and which do not interfere too much with the easy and independent adjustment of the adjustable effective length struts.

Figure 5:
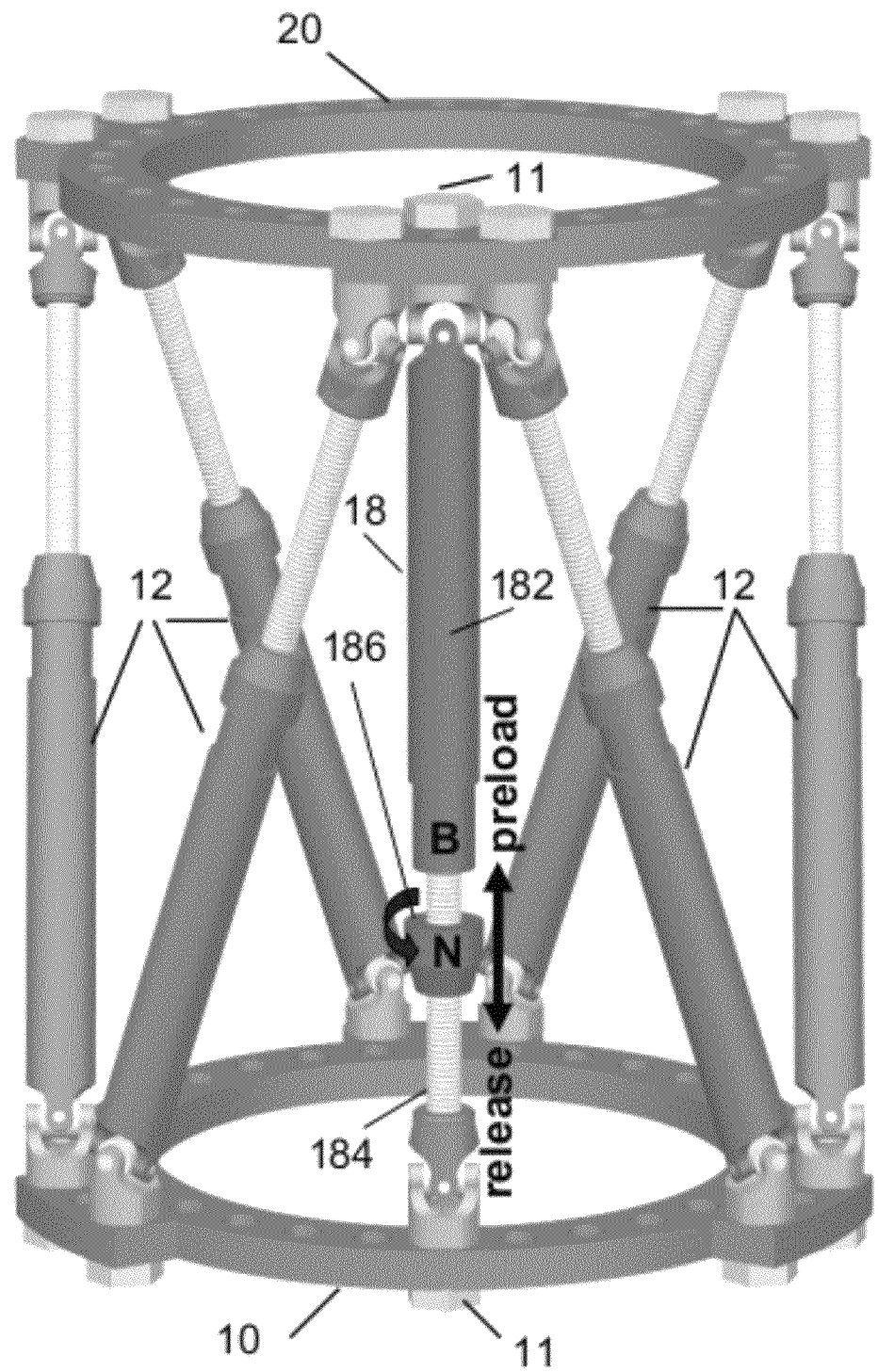
FIG. 5 is a schematic diagram illustrating the operation of a preloading strut having adjustable minimum length.

In accordance with one embodiment of the present invention, FIG. 5 illustrates how the need for simultaneous adjustment of the preload member and the actuator can be avoided by using a preload strut 18 which is similar to the adjustable length struts 12, but has been modified so that it can only be loaded in compression. Preload strut 18 can easily be created by eliminating the retaining ring 129 (FIG. 2B) which normally holds the threaded collar 128 in a relatively fixed axial position relative to the cylinder 126 in adjustable struts 12. Without any axial retention means, the threaded collar 186 of preload strut 18 will be free to move (together with the threaded rod 184) axially away from the end of the outer strut tube 182. In the illustrated embodiment, the preload strut 18 can be adjusted to have any desired minimum length (within some range) and can accommodate compression (i.e., shortening) forces, but is free to extend out to a maximum length with essentially no tension forces. In the particular preload device 18 illustrated in FIG. 5, when the rotating nut "N" (also collar 186) is "jammed" up against the body B (also tube 182), then the preload actuator will extend slightly until any clearance or backlash is removed from the adjustable struts 12 on either side. But if the adjuster nut N (186) is simply backed away a few turns, then strut 12 on either side can be adjusted independently, just as when there was no preload actuator 18 present.

In the illustrated embodiment, the amount of preload force is generally proportional to the torque which is applied to tighten nut 186 against body tube 182. It will be appreciated to those skilled in the art, however, that there are many ways which could be used to limit the maximum preload force. One such approach for limiting the maximum preload force would be the use of a one-way torque-limiting slip clutch on nut N, similar to the approach used on modern automotive gasoline caps to limit the available tightening torque without limiting the torque available to remove or loosen the threaded cap.

The assembly shown in FIG. 5 is meant to illustrate how preload element 18 can be used to remove the clearances from two adjacent adjustable struts 12. As previously noted, either of the adjacent struts 12 can be independently adjusted whenever the preload adjustment nut 186 is adjusted away from tube 182 of preload strut 18. An important additional feature of the illustrated assembly results whenever the ends of preload strut 18 are positioned at, or very near, the midpoints between the ends of neighboring struts 12. In such a preferred configuration, where the preload strut between two adjustable struts is positioned at the convergence of a pair of adjustable effective length struts so that it does not significantly add to the kinematic constraints afforded by the struts 12 on the allowable orientation of the upper frame 20 relative to the lower frame 10, the four adjustable struts 12 which are not the immediate neighbors of preload strut 18 can be independently adjusted even when the preload strut 18 is providing preload to the two neighboring struts 12.

Figure 6:
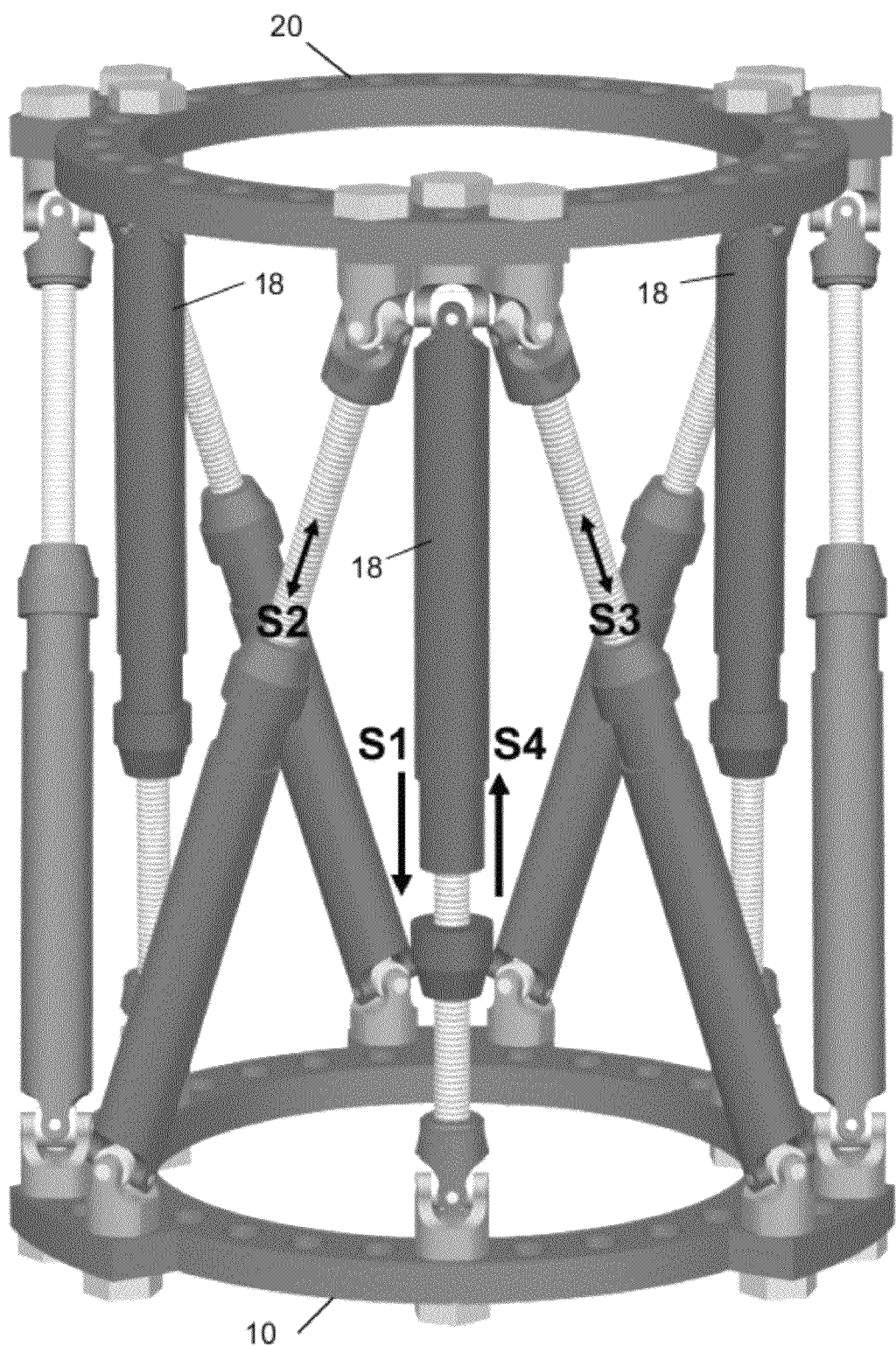
FIG. 6 is a schematic diagram illustrating the sequential process of adjusting the length of two adjustable effective length struts and one adjustable minimum length preload strut.

FIG. 6 illustrates a fully populated version of a fixator device of a preferred embodiment of the present invention, where three preload struts 18 are used to preload all six adjustable struts 12. Each individual preload strut 18 is positioned between a pair of adjustable struts 12, and provides preload to that pair of struts. It should be apparent to those skilled in the art, that for small adjustments of the strut 12 lengths when the preload struts 18 are positioned sufficiently close to the ideal locations described previously in FIG. 3, each preload strut 18 only prevents the shortening of an immediately neighboring adjustable strut. Lengthening of a neighboring strut will have the effect of removing the preload, and can be done without first loosening the preload device. Furthermore, lengthening or shortening of any non-neighbor struts will not be significantly affected by the preload generated by a non-neighboring preload strut. Therefore, it is possible to maintain maximum frame stability while making desired frame adjustments by only loosening one preload strut at a time and adjusting only the neighboring struts 12 before re-applying the preload from strut 18. In other words, the actuation of a preload strut 18 constrains independent adjustment of adjacent adjustable effective length struts 12 while not substantially constraining independent adjustment of non-adjacent adjustable effective length struts 12. The preferred adjustment operation for maximum stability (i.e., minimum positional uncertainty during adjustment) is illustrated schematically in FIG. 6 and can be described as the following:

Step S1) Release one of the preload nuts on one of the three preload struts 18.

Step S2) Shorten or lengthen the strut 12 on one side of the preload strut 18 to the desired length.

Step S3) Shorten or lengthen the strut 12 on the opposite side of the preload strut 18 to its desired length.

Step S4) Tighten the preload nut on the selected preload strut 18 to preload the two neighboring struts 12 in their new positions.

Repeat steps S1-S4 for each of the remaining two "triplets" comprising one preload strut 18 and two adjacent adjustable effective length struts 12.

In some cases, it may not be possible to position the ends of the preload struts 18 near the ideal points described in FIG. 3, and the resulting non-ideal positioning of the preload struts may create kinematic binding which makes it difficult to adjust some strut lengths even when the neighboring preload strut is disengaged. In those cases, or simply when it may be more convenient to loosen all preload struts first, an alternative adjustment process would be to release the preload nuts 186 on all three preload struts 18, then shorten or lengthen each of the six struts 12 to achieve the desired length, and then re-tighten the preload nuts 186 on all three preload struts 18.

Adjustable Compliance

The medical literature (e.g., Wheeless' Textbook of Orthopaedics, available online at www.wheelessonline.com) indicates that bone fracture healing and bone regeneration is significantly affected by the level of mechanical rigidity that is provided by fixation devices during the healing process. More specifically, it is generally believed that the optimal level of fixation rigidity varies during the fracture healing process, with maximum rigidity (i.e., minimum compliance) generally being most appropriate during the initial primary healing or callous formation phases, and with progressively lower rigidity (i.e., higher compliance) being most appropriate during the later callous remodeling phase when load sharing between the bone and the frame is required. Current orthopedic fixation devices, such as the Taylor Spatial Frame, have manufacturing tolerances that significantly limit the maximum stiffness that can be achieved for small displacements, and they provide no controllable means for reducing the stiffness (i.e., increasing the compliance) during later healing stages.

The increased maximum stiffness which is desirable from an orthopedic healing perspective has been provided in the previously described embodiments via the incorporation of pre-loading elements 18 to substantially remove the effect of manufacturing tolerances and necessary clearances in an assembly comprising a plurality of adjustable effective length struts 12 which define the spatial orientation of an upper frame 20 relative to a lower frame 10. In accordance with additional embodiments described herein, we now teach methods of adjustably decreasing the stiffness (i.e., increasing the compliance) of the orthopedic fixator to values below that of the maximum stiffness achieved using the structure shown in FIG. 6.

Figure 7A:
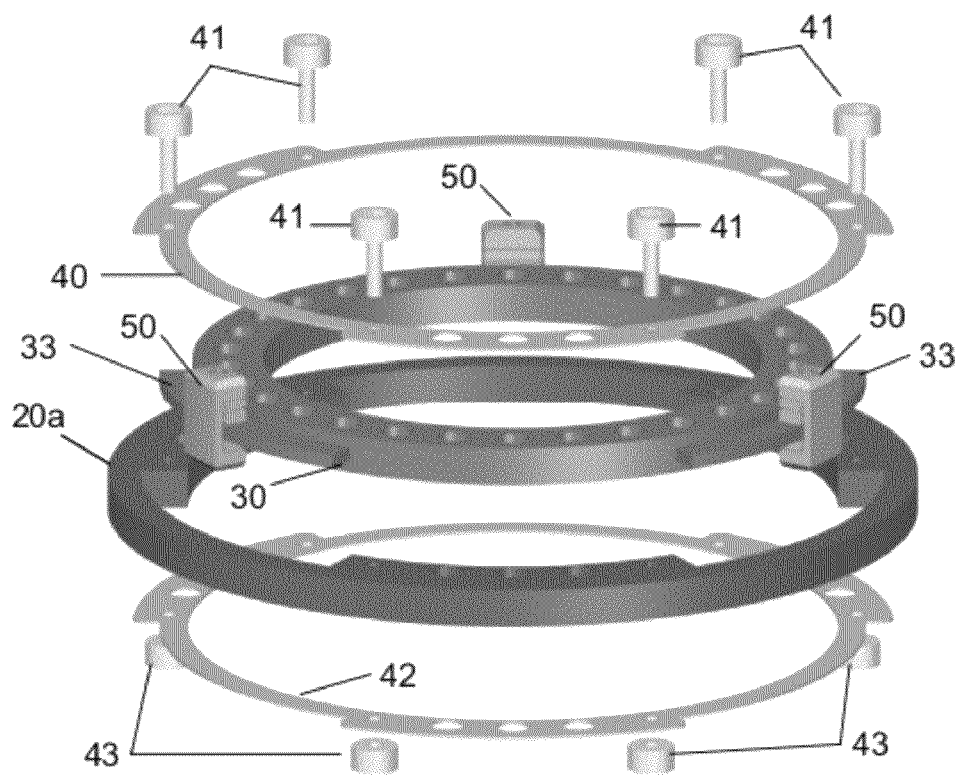
FIG. 7A is an exploded view of an adjustable compliance attachment portion used in an embodiment of the invention.
Figure 7B:
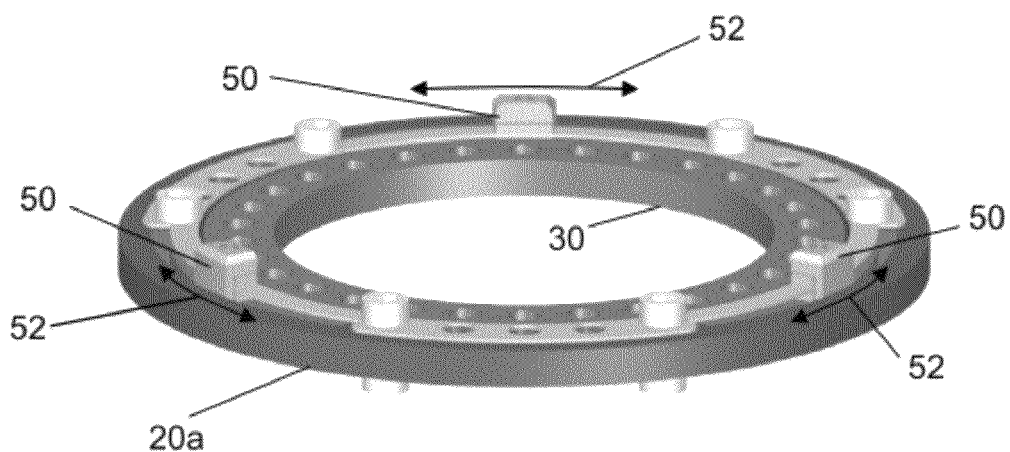
FIG. 7B is an assembled perspective view of the adjustable compliance portion of FIG. 7A.
Figure 7C:
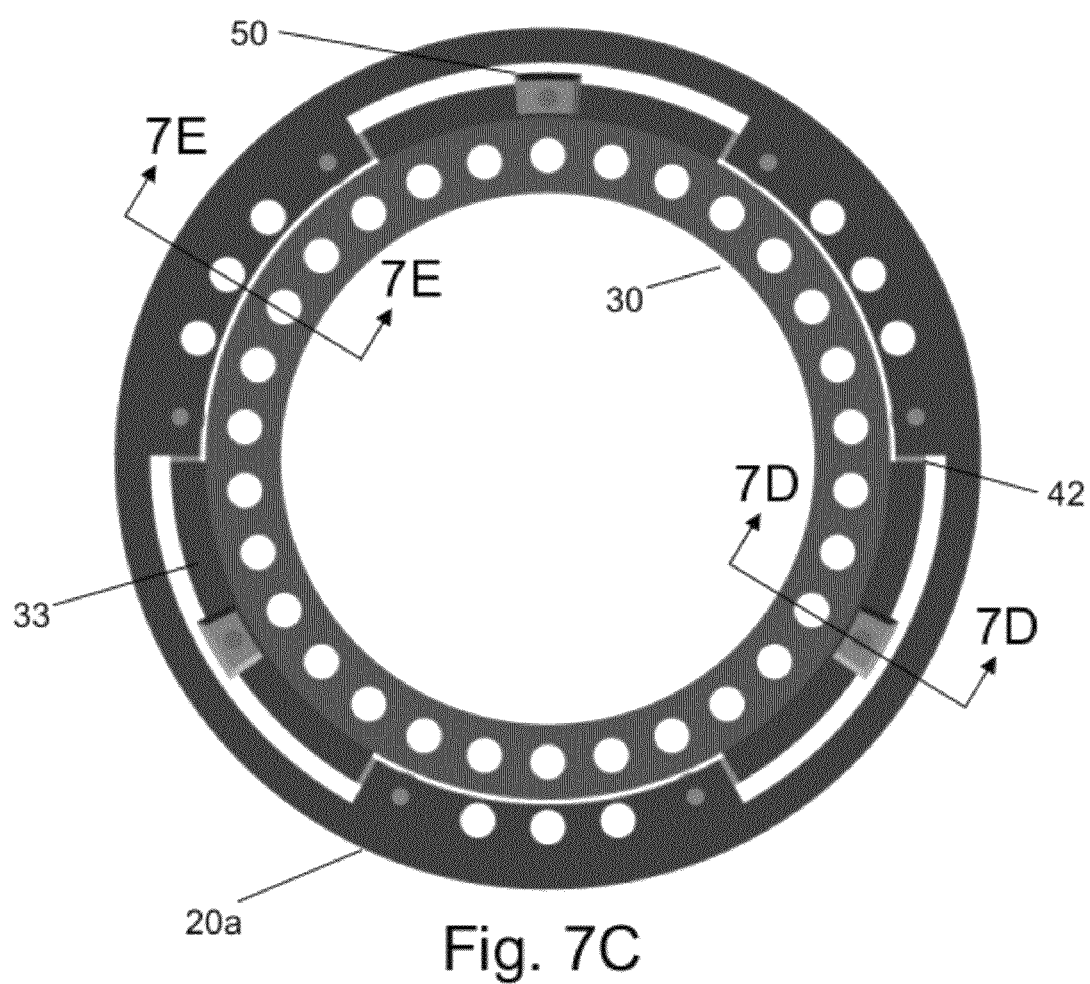
FIG. 7C is a top view of a portion of the adjustable compliance attachment portion if FIG. 7B with the top spring removed for clarity.
Figure 7D:
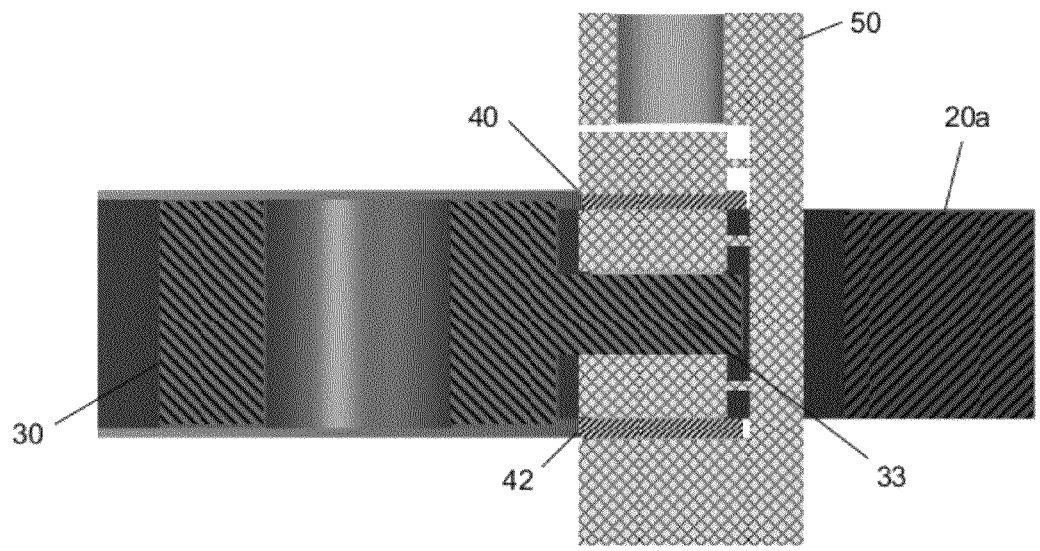
FIG. 7D is a section taken through line 7D-7D of FIG. 7C with the top spring included.
Figure 7E:
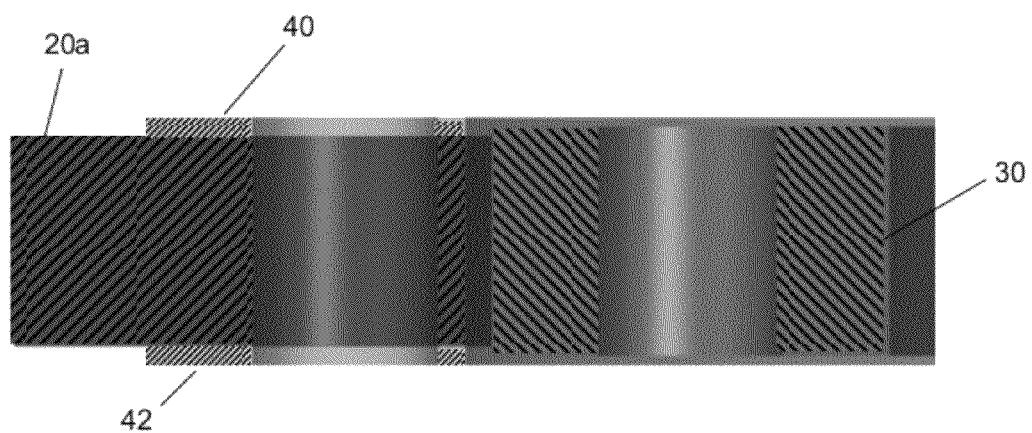
FIG. 7E is a section taken through line 7E-7E of FIG. 7C with the top spring included.

In FIG. 6, the upper frame 20 is connected directly to the adjustable length struts 12 as well as to mounting structures attached to a bone element (not shown). In accordance with an additional embodiment of the invention, there is shown in FIGS. 7A-7E, where FIG. 7A is an exploded view, FIG. 7B is an assembled view, FIG. 7C is a top view and FIGS. 7D and 7E are cross-sectional views, an additional preferred embodiment of a fixator device comprising an upper plate 20a (sometimes referred to as upper ring 20a) that is flexibly attached to an inner upper plate 30 (sometimes referred to as inner upper ring or inner ring 30) which is, in turn, connected to mounting structures attached to a bone element (not shown). In the particular device illustrated, the flexible or compliant attachment between the upper plate 20a forms an outer ring which surrounds the inner upper plate 30. One or more spring plates 40, 42 are clamped to the upper plate 20a using bolts 41 and nuts 43, or any other suitable means as would be known to those skilled in the art. Inner ring 30 has radially extending wing segments 33 which support clamp elements 50. Clamp elements 50 are designed to clamp a region of the spring plate(s) 40, 42 in addition to the radial extension 33 of the inner ring 30. FIGS. 7C-7E illustrate the engagement of the rings 20a, 30 with the plates 40, 42 along various sections of the rings 20a, 30. The upper ring 40 is not shown in FIG. 7C only for purposes of clarity, even though it is represented in the sectional views FIGS. 7D and 7E. Furthermore, the inner and outer rings 20a, 30 are concentric in the present embodiment, although they may be positioned in a non-concentric manner if desired.

Figure 8A:
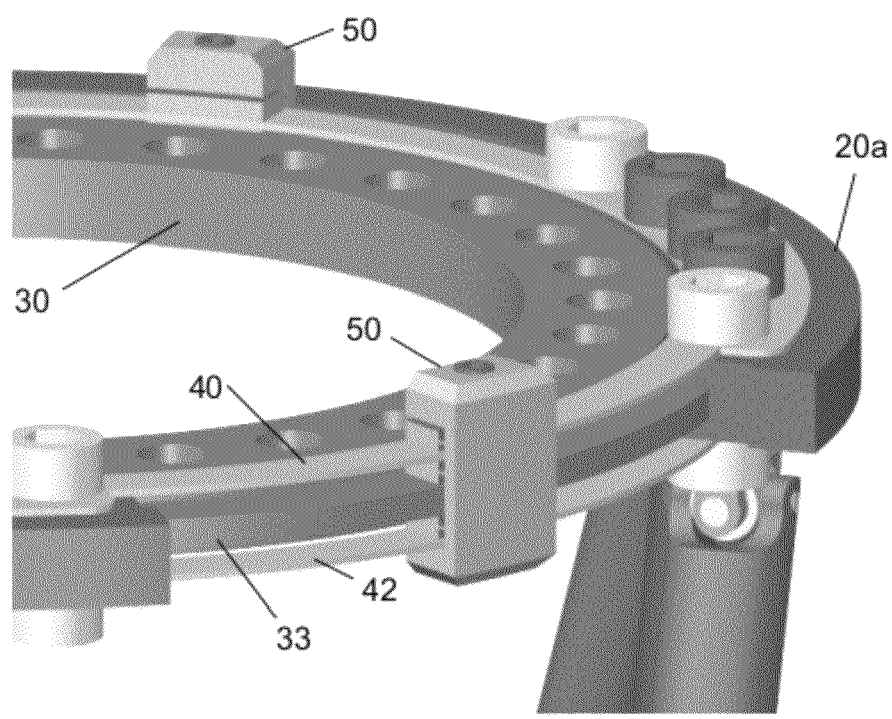
FIG. 8A is a perspective view of an adjustable parallelogram spring portion of an embodiment of the invention with a portion of the outer ring removed for clarity.

In addition, while the upper plate 20a is shown attached to the lower frame 10 as shown more clearly in FIG. 8A among others, it will be appreciated that a reverse construction could be contemplated where the inner ring or plate 30 is attached to the lower frame 10 and the outer ring 20a is compliantly attached to the inner ring 30, where the structural features and functions of the outer ring 20a and inner ring 30 as described herein are essentially reversed. Alternatively, for example, the outer ring 20a could still be attached to the lower frame 10, but the outer ring 20a has inwardly projecting radial features and the clamps 50 fix the spring plates 40, 42 to the outer ring 20a. Thus, instead of the inner ring 30 having radially extending wing segments 33 which support clamp elements 50, with clamp elements 50 designed to clamp a region of the spring plate(s) 40, 42 in addition to the radial extension 33 of the inner ring 30, the outer ring 20a would have inwardly extending radial extending wing segments which support clamp elements 50, and the clamp elements 50 would be designed to clamp a region of the spring plate(s) 40, 42 in addition to the radial extension of the outer ring 20a. So, not only can the inner and outer rings 30, 20a respectively be reversed with respect to which one is connected to the lower frame 10, but also the selection of which ring is fixed to the spring plates 40, 42 and which ring is clamped to the spring plates can also be reversed, regardless of which ring is connected to the lower frame 10. Thus, the structural embodiments illustrated herein are not meant to be interpreted in a limiting sense as set forth below.

Figures 11A, 11B:
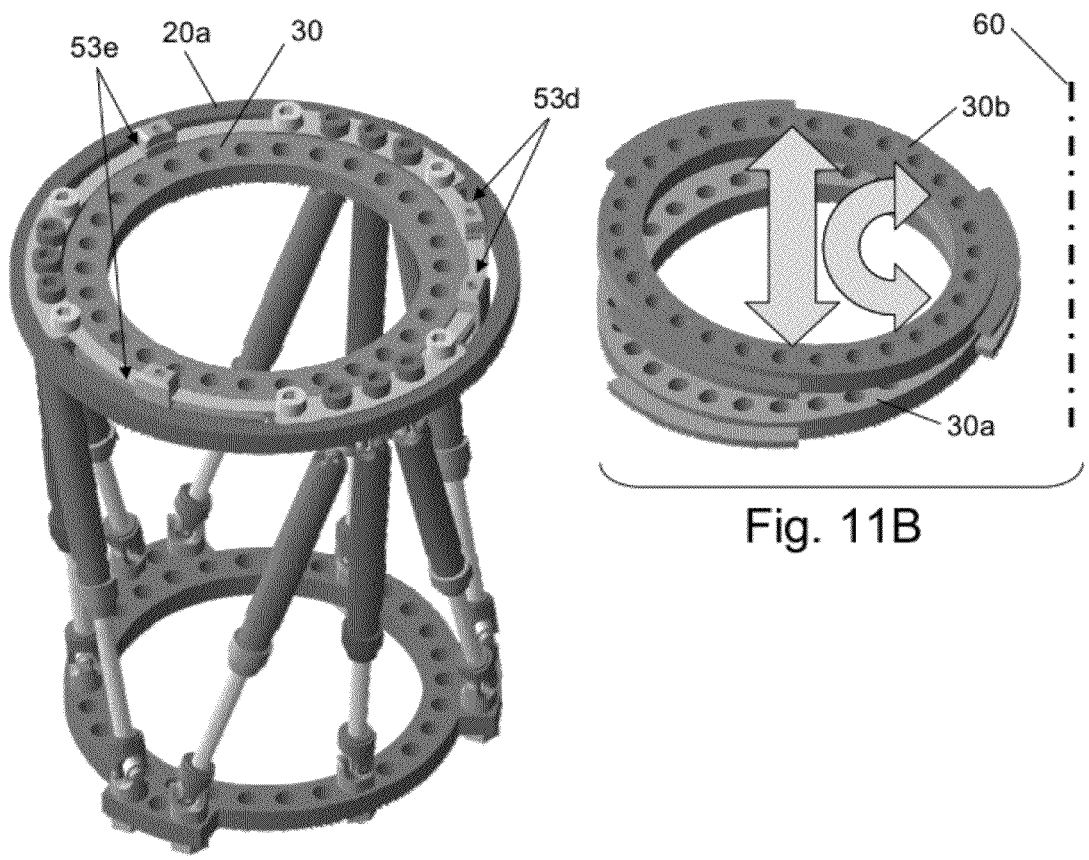
FIG. 11A is a perspective view of an embodiment of the invention adjusted to provide non-axial effective compliance.
FIG. 11B is a schematic diagram of a portion of an embodiment of the invention illustrating the remote center of rotation and non-axial effective compliance which is achievable.
Figure 12:
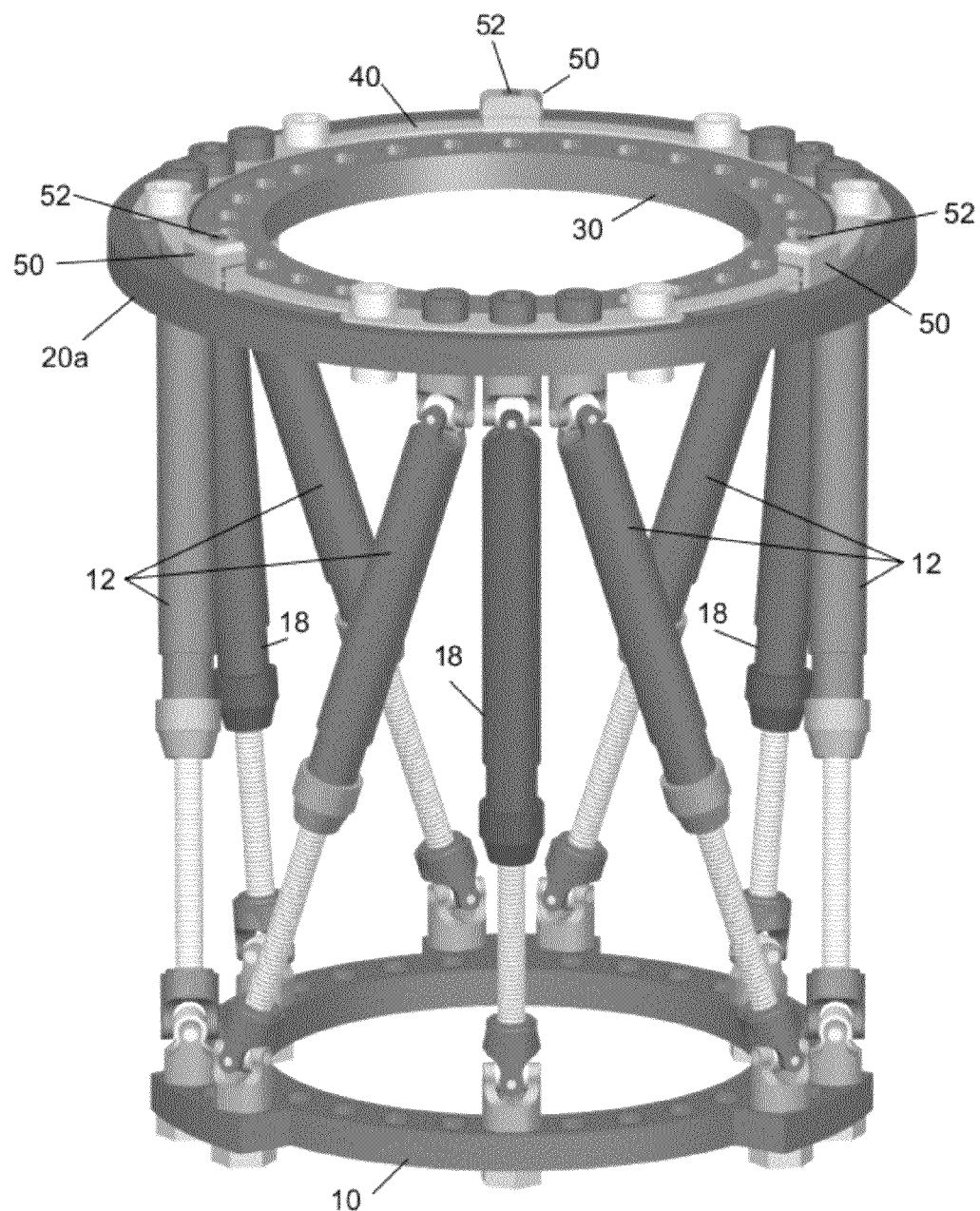
FIG. 12 is a perspective view of one embodiment of the invention.

The adjustable compliance provided through the use of inner and outer rings as illustrated herein, for example, can be utilized on a fixator device having pre-load elements 18 described above and as shown in FIG. 12. Alternatively, the prior art design of FIG. 1 without preloading could be further incorporated with adjustable compliance features as described herein for purposes of improving the benefits and features of the prior art fixator device with the benefits of adjustable compliance. Thus, the benefits and features of preloading and adjustable compliance can be realized individually or jointly. FIG. 12 illustrates one embodiment comprising multiple benefits as described herein, including both preloading and adjustable compliance. For purposes of explanation, the embodiments of FIGS. 7A-11B will be representative of the fixator device shown in FIG. 12, it being understood that other configurations are possible.

An important aspect of the illustrated embodiment is the ability for the multiple clamps 50 to be positioned at various points around the periphery of the radial extensions 33 of the inner ring 30, such that the attachment of the spring elements 40, 42 preferably occurs along a circumference defined along the outer ring 20a. If the clamps are positioned midway along the free length of spring elements 40, 42, then two equal length flexural spring regions are formed on opposite sides of the clamp 50. If, however, the clamp is positioned very close to a point where the spring element 40 or 42 is mounted or clamped to plate or ring 20a, then the length of the unsupported spring element to one side of the clamp 50 is smaller than the unsupported length of spring element to the opposite side of the clamp 50. While the sum of the two unsupported spring lengths is fixed by the geometry of the spring plate 40 or 42, the position of the clamp 50 determines how that total length is divided into two complementary segment lengths.

As is known to those skilled in the art, the bending stiffness of a plate spring is proportional to the cube of the length of the spring. The result of this non-linear relationship between stiffness and length means that two springs of equal length will have a lower stiffness than one shorter and one longer spring that add up to the same total length. In other words, two springs which are each two centimeters long each will combine to have a lower stiffness than one centimeter long spring together with one three centimeter long spring. As one spring approaches zero length and the other spring grows by the same amount, the total stiffness will continue to increase, up to the theoretical limit where one spring has zero length and nearly infinite stiffness. Furthermore, this nonlinear force-displacement is such that a displacement of the inner ring 30 relative to the outer ring 20a increases by less than a factor of two when an external force applied to the compliant attachment increases by a factor of two.

In accordance with the present invention, the effective stiffness of the elastic mounting between plates 20a and 30 can be adjusted over a wide range of values simply by changing the position of the clamp elements 50. When the clamps 50 are positioned midway along the length of spring plates 40, 42 (in between the points where spring plates 40, 42 are mounted to outer ring 20a), as shown in FIG. 7B, then the total effective stiffness of the elastic mounting between plates 20a and 30 is minimized. If one or more of the clamps 50 is moved closer to any of the points where spring plates 40, 42 are attached to outer ring 20a, then the stiffness increases. And if the clamps 50 are placed immediately next to the locations where spring plates 40, 42 are attached to outer ring 20a, then the stiffness is maximized (i.e., the compliance is minimized).

Having observed the details of the effect of dividing a fixed length of spring into two complementary spring lengths, attention may now be given to the details of the spring plates themselves and the clamps elements 50 used to fix a region of the spring plate 40 to the radial extension 33 of the inner ring 30. FIG. 8A shows a close-up view of the outer ring 20a, a segment of which is removed for clarity, the inner ring 30, an upper spring plate 40, and a lower spring plate 42, along with the movable clamp elements 50. In accordance with one aspect of the invention, both a lower spring plate 42 and an upper spring plate 40 can be used to flexibly attach outer plate 20a to inner plate 30. As will be understood to one skilled in the art, the use of two parallel springs mounted some reasonable distance apart, but clamped at the same position so that they have the same free length, will create a parallelogram spring assembly which has relatively low stiffness against vertical translation and against rotation around the axis of the springs, but provides high stiffness against translation in the plane of the rings and rotation around the axes orthogonal to the spring axis. Since, in the embodiment shown, the three sets of springs positioned around the ring 20a have different axes, the combination of springs provides compliance (low stiffness) primarily for vertical translation only.

Figure 8B:
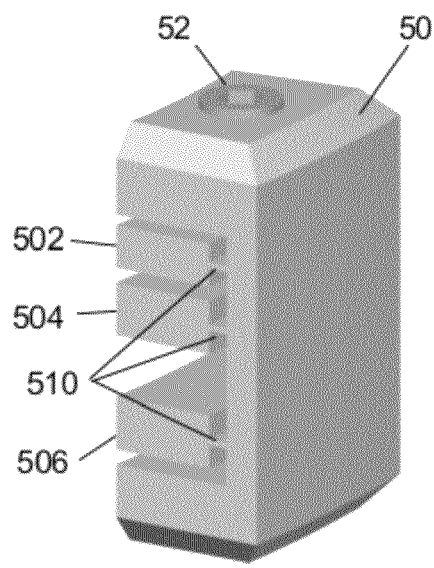
FIG. 8B is a perspective view of an adjustable position clamp portion used in an embodiment of the invention.

The clamping of a portion of the spring plates 40 and 42 can be accomplished in many ways. It is preferable, however, for the clamp assembly to be easily repositioned and to have a minimum number of separate elements which have to be positioned properly. This is accomplished in one embodiment of the present case as illustrated in FIG. 8B, which shows a single clamp element 50, comprising integrally formed spacer elements 502, 504, and 506 attached to the main body of clamp 50 through thin flexible flexure elements 510. The spacer elements fill the gaps between the spring plates 40 and 42 and the radial wing extension 33 of the inner ring 30, so that actuation of a single set-screw 52 or the like can be used to clamp a region of both spring plates 40 and 42 firmly against the radial wing extension 33 of inner ring 30. Thus, in the present embodiment, the effective complementary lengths of the dual parallelogram springs which are formed on each side of clamp 50 can be easily adjusted by loosening screw 52, sliding the clamp 50 to a new circumferential position around the inside perimeter of ring 20a, and then re-tightening the screw 52. By always having two clamps tightened when one is loosed, the inner ring 30 will be prevented from rotating or shifting laterally. In addition, alignment markings or scales of various types can be provided on one or more of elements 20a, 30, 40, or 42 to visually indicate specific locations for clamps 50 and (optionally) the resulting compliance associated with those clamp locations.

Figure 9:
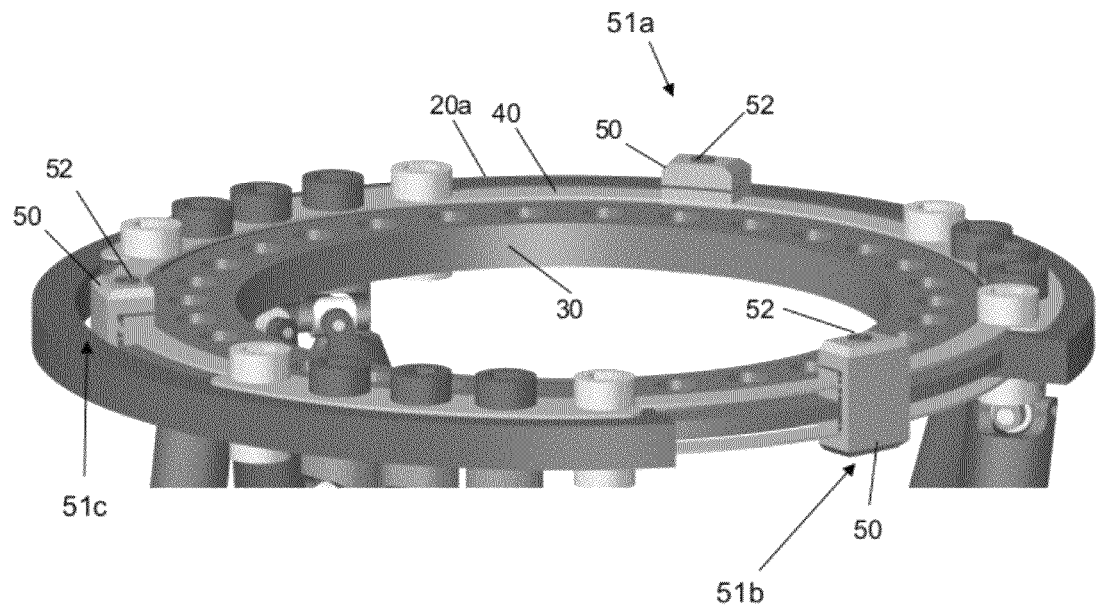
FIG. 9 is a schematic diagram illustrating one embodiment of a sequential process of adjusting the structural compliance.

In the embodiment illustrated in FIG. 9, the axial compliance of the elastic mounting between outer plate 20a (a portion of which is removed for clarity) and inner plate 30 can be adjusted without ever completely decoupling plates 20a and 30, through the following recommended adjustment sequences. The first sequence illustrated in FIG. 9 by reference number 51a comprises loosening the clamp screw 52 on the first of three clamps 50, sliding the first clamp 50 to the desired location to provide the appropriate stiffness and then tightening the clamp screw 52 on the first clamp 50. The second sequence illustrated in FIG. 9 by reference number 51b comprises loosening the clamp screw 52 on the second of three clamps 50, sliding the second clamp 50 to the desired location to provide the appropriate stiffness and tightening the clamp screw 52 on the second clamp 50. The third sequence illustrated in FIG. 9 by reference number 51c comprises loosening the clamp screw 52 on the third of three clamps 50, sliding the third clamp 50 to the desired location to provide the appropriate stiffness and tightening the clamp screw 52 on the third clamp 50. Of course, the order of sequences 51a-51c can be modified as desired.

Various details of the mounting and clamping of the springs to the outer ring 20a can be changed without departing from the spirit of the invention, with the addition of outer clamping plates being one possible modification to improve the mounting stiffness. The clamps are shown as one-piece elements fabricated using a wire-EDM process to form spacers and a force spreading block that are free to float vertically by a small amount to account for tolerances, but which are integral to the clamp and thus forced to translate with the block. Other clamp designs and configurations are possible, including, but not limited to, those with free floating spacer elements, etc., or spacers which are constrained by other means (e.g., pins or other geometry) to translate with the clamp block during installation/adjustment.

Figure 10:
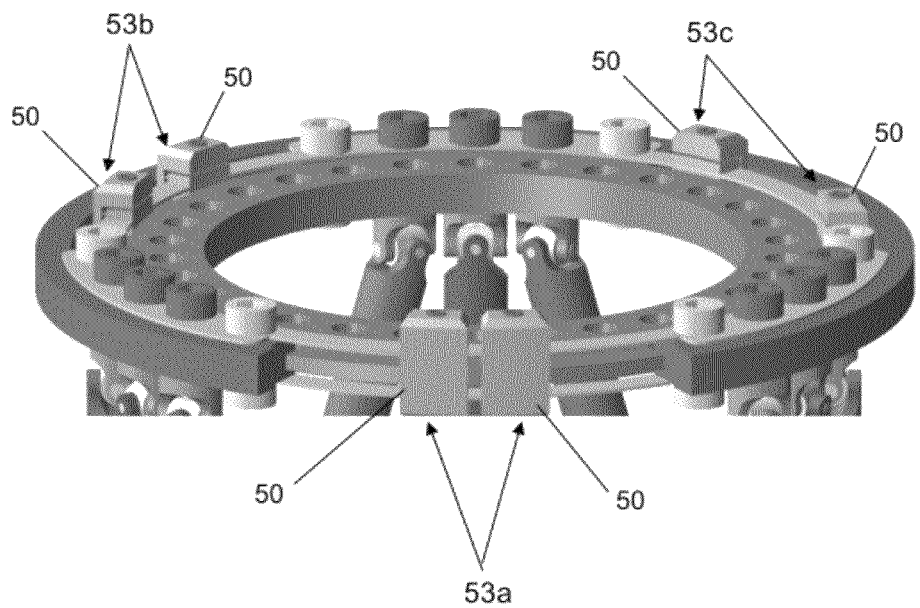
FIG. 10 is a perspective view of an alternative arrangement of adjustable position clamps to control the local structural compliance.

FIG. 10 illustrates another embodiment of the invention where a larger number of clamping elements 50 is used. In the particular embodiment illustrated, each of the three circumferential regions of spring plates 40 and 42 are clamped with two clamps 50. In this case, the free length of the dual parallelogram springs can be equal. These dual clamps are shown in various potential desirable configurations, including: a minimum-stiffness (i.e., maximum compliance) case 53a where the two clamps 50 are both close to the middle of the flexing portion of spring plates 40 and 42; an intermediate stiffness case 53b where the two clamps are symmetrically positioned some distance away from both the center of, and the mounting region of, the flexing portion of spring plates 40 and 42; and the maximum stiffness case 53c where both clamps 50 are positioned very near the location where spring plates 40 and 42 are attached to outer ring 20a.

In some medical circumstances, it may be desirable to create non-axial compliance, i.e., a remote center-of-rotation, between the inner ring 30 and the outer ring 20a. In accordance with the present invention, such non-axial compliance can be created as shown in FIG. 11A, where the axial stiffness of the three spring regions positioned around the periphery of the circular ring plates is intentionally adjusted to be unequal. By positioning some clamps for higher stiffness (clamp pair 53d) than other clamps (clamp pair 53e), it is possible to modulate the effective compliance to create a remote center of motion. This could be useful, for example, if the axis of the bone is perpendicular to the plane of the mounting ring, but the fracture plane is not orthogonal to the bone axis. In the example shown in FIG. 11A, two clamps (53d) are used to create high stiffness in one of the three spring sectors, while the clamp positions in the other two sectors are adjusted to provide lower stiffness. The resulting non-uniform axial stiffness of the ring support points will result in a rocking motion under loading, and this combination of axial deflection plus rocking may better resist separation of an angled fracture plane. As illustrated in FIG. 11A, two clamps (53d) are positioned so as to create relatively short spring elements at the right-hand side of the spring plates so that the axial stiffness at that point will be higher than that provided by the single, centrally located clamps (53e) at the other two positions approximately one hundred and twenty degrees around the ring. The net effect of this non-uniform spring stiffness is to create a non-axial compliance and a remote-center-of-rotation axis 60 effect by which the inner ring 30 will not respond to an axial load with direct axial motion, but will instead, respond to an axial load with a combination of axial motion plus some tilting rotation about an axis 60 somewhere to the right of the assembly, as illustrated schematically in FIG. 11B with the movement of the inner ring 30 between a first position 30a and a second position 30b. It should be appreciated that this movement is illustrated in FIG. 11B to a greatly exaggerated extent, where in practice no portion of any of the inner ring extensions should translate vertically by more than the provided clearance, which is +/−2.5 millimeters in this embodiment.

An additional feature of the invention is the optional ability to provide non-linear compliance between the upper inner ring 30 and the upper outer ring 20a. A spring is said to be linear if a doubling of the external force produces a doubling of the deflection. For best bone healing, especially during secondary healing and callus consolidation, it is important that the healing bone experience some external loading, but it is also important that the healing bone joint be protected from excessive external loads. A non-linear force deflection curve is thus desirable, whereby a larger fraction of small external loads is transferred to the bone, but only a smaller fraction of very large external loads is transferred to the bone. In the preferred construction shown in FIGS. 7-12, such a non-linear force deflection curve is naturally produced as a result of the use of spring elements where both ends of the springs are fixed. As is known by those skilled in the art, a cantilever spring element produces a largely linear restoring force in response to an applied deflection, but a spring plate or membrane which is held at both ends produces a non-linear restoring force in response to an applied deflection somewhere along its length. More specifically, the equation defining the force-deflection curve contains a term proportional to the cube of the deflection. Thus, the spring gets progressively stiffer as the deflection increases, which is precisely what is desired to help protect the bone from large external forces while still transmitting a significant fraction of small external forces.

The same analysis holds true for the parallelogram spring construction created through the use of both an upper spring plate 40 and a lower spring plate 42. While a single parallelogram flexure with a free end would behave linearly (for reasonably small deflections), the fixed mounting of the ends of the two parallelograms on either side of the clamp creates a membrane spring effect, and thus the stiffness will increase as the deflection is increased. As noted previously, membrane force-deflection expressions have a cubic term in the force-deflection curve and therefore, this design naturally provides lower stiffness for small loads, and higher stiffness for higher loads. If nonlinear stiffness is not desired for some reason, the spring plates described in this invention can be modified so that one end is free. In that case, the membrane forces will be eliminated and the spring will generate a linear force-deflection profile.

In a further embodiment, each of the spring plates 40 and 42 can be replaced by a plurality of plates. The ability to use a larger number of thinner springs, instead of a smaller number of thicker springs, for example, enables a spring designer skilled in the art to provide a wide range of stiffnesses, while also accommodating a desired amount of deflection with an acceptable amount of material stress. The number and thickness of the spring rings used determines the available stiffness range for each spring section, and the position of the clamps 50 determines the selected level of compliance within that available range.

Yet another important safety feature of the invention is the ability to limit the maximum motion of the inner ring 30, and thus to limit the maximum motion of the attached bone segment (not shown). In accordance with the construction of the embodiment illustrated in FIGS. 7-12, the motion of the inner ring 30 is naturally limited in all directions, regardless of the stiffness of the springs and the clamp position. The inner ring 30 is constrained by clearances with the outer ring 20a against large radial motion and circumferential rotation. Vertically, each radial extension of the inner ring 30 is independently limited by the distance between the radial extension surfaces and the top and bottom surface of the outer ring 20a to which the springs are mounted. These clearances (preferably on the order of 2.5 millimeters each in the embodiment shown) can be unequal if desired, so extension motion can be limited to a different value than compression motion. In any case, vertical motion larger than the clearance would require shearing one or more springs near their connection to the outer ring 20a.

An important set of safety features of the invention is the provision of mechanical redundancy in all critical areas, which prevents any single failure of a mechanical component from leading to a catastrophic failure of support. If a preload strut 18 fails, the external loads will be supported by the adjustable effective length struts 12, although with some loss of positioning precision and rigidity. If an adjustable effective length strut 12 fails, external compressive loads will be supported by neighboring preload struts 18. Although a large extensional load could still cause a large deflection at the bone, even this theoretical failure mode could be addressed by a simple modification of the preload strut 18 so that the adjustable nut 186 is constrained by a retaining ring in an overly wide slot such that retaining nut 186 can only move axially some reasonable maximum distance, preferably on the order of a few millimeters, relative to the outer tube 182 of the preload strut 18.

As a further example of mechanical redundancy which prevents single points of failure from causing potentially catastrophic failure to maintain acceptable bone positions, each spring plate preferably comprises multiple independent flexing regions and multiple independent points of fixation to both the outer ring 20a and the inner ring 30. If the spring fails at any one point, the motion of the system is still limited by other spring regions and by the mechanical limit stops created by the nesting of the radial extensions 33 of the inner ring 30, each of which is confined inside the outer ring 20a, underneath the upper spring 40, and above the lower spring 42. Similarly, if a clamp element 50 or a clamping screw 52 fails, the inner ring will still be supported and constrained to prevent excessive motion.

One process for orthopedic fixation of two skeletal elements during healing comprises fixing a position of a first skeletal element relative to a second skeletal element using an orthopedic fixator with adjustable compliance as discussed above, adjusting the position and the compliance of the orthopedic fixator to minimize motion of the skeletal elements during a first phase of healing, and increasing the adjustable compliance of the fixator in at least one direction during a second phase of healing. A further process comprises increasing the adjustable compliance of the fixator in at least one direction after the second phase of healing.

Having thus described several embodiments of the present invention, it will be appreciated that such embodiments represent an orthopedic fixation solution having many or all of the following beneficial characteristics:

Precision—the ability to adjust the relative position of two bone segments in six degrees of freedom to within a very small degree of error.

High Maximum Stiffness—the ability to maintain any adjusted position with very little motion occurring in any direction as a result of external forces.

Adjustable Compliance—the ability to controllably reduce the effective fixation stiffness below a maximum level during select healing phases. Although step-wise stiffness control may be acceptable, a preferred solution would allow for continuous stiffness adjustment between some maximum and minimum level.

Anisotropic Compliance—the ability to provide higher compliance (i.e., lower stiffness) along some direction (typically the bone axis or perhaps the direction perpendicular to a fracture plane) than in all other degrees of freedom.

Nonlinear force-deflection curve—for any overall stiffness level selected, the provision of a lower incremental stiffness at smaller loads can enable significant load sharing to the bone at low loads, while a higher stiffness at larger deflections ensures that a larger fraction of abnormally high input forces are transferred to the fixation frame instead of the bone.

Motion limit stops—the incorporation of physical constraints designed to limit total possible bone motion to a safe maximum level regardless of the load applied and the frame stiffness adjustment. Most preferably, it should also be possible to limit the maximum deflection in one direction independently of the opposite direction, so that maximum bone extension can be limited to a different value than maximum bone compression, if desired.

Structural redundancy—the design of structural elements and the duplication of key parts such that failure of any single component will not result in excessive displacement of the bone.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

I claim:

1. An orthopedic fixator comprising:
   a) a first frame and a second frame adjustably attached to the first frame;
   b) a third frame connected to the first frame; and
   c) a compliant attachment having adjustable compliance defined between the first and third frames;
   d) at least one spring plate attached at a first location to one of said first frame and said third frame and attached at a second location to the other of said first frame and said third frame; e) the at least one spring plate is attached at the second location by at least one positionable clamp, wherein the position of the at least one positionable clamp can be varied to change a distance between the first and second locations; and f) wherein the at least one positionable clamp is movable from a first position closest to the first location, which results in minimum compliance, to a second position spaced from the first location, which results in increased compliance between the first and third frames.

2. The orthopedic fixator of claim 1, wherein the first and third frames are concentric.

3. The orthopedic fixator of claim 1, further comprising a plurality of struts connecting the first frame to the second frame to fix the position of the first and second frames to within a positional tolerance, and at least one preload element disposed between the first and second frames for preloading at least one of the struts to substantially reduce the positional tolerance.

4. The orthopedic fixator of claim 1, wherein the second location further comprises a radial extension of the third frame.

5. The orthopedic fixator of claim 4, wherein the first and second locations are circumferentially aligned.

6. The orthopedic fixator of claim 1, further comprising a plurality of positional clamps.

7. The orthopedic fixator of claim 1, further comprising at least a pair of spring plates positioned on opposite sides of the first frame to create at least one parallel flexure support.

8. The orthopedic fixator of claim 1, further comprising physical stops for limiting a displacement of the third frame relative to the first frame to a maximum distance, wherein the maximum distance is independent of the degree of compliance provided by the compliant attachment between the first and third frames.

9. The orthopedic fixator of claim 8, wherein the maximum displacement of the third frame relative to the first frame in a direction towards the second frame is different than the maximum displacement of the third frame relative to the first frame in the direction away from the second frame.

10. The orthopedic fixator of claim 1, wherein one of said first frame and said third frame further comprises angular openings and the other of said first frame and said third frame comprises radial extensions that extend within the angular openings to prevent the first and third frames from rotating relative to each other.

11. The orthopedic fixator of claim 1, further comprising:
multiple adjustable compliant attachments of the first frame to the third frame, the compliant attachments being independently adjustable to create a remote axis of rotation for the third frame.

12. An orthopedic fixator comprising a) a first frame and a second frame adjustably attached to the first frame; b) a third frame connected to the first frame; c) a compliant attachment having adjustable compliance defined between the first and third frames; and d) at least one spring plate attached at a first location to one of said first frame and said third frame and attached at a second location to the other of said first frame and said third frame; e) wherein the at least one spring plate is attached at the second location by at least one positionable clamp, wherein the position of the at least one positionable clamp can be varied to change a distance between the first and second locations; and f) wherein the compliant attachment provides a nonlinear force-displacement response whereby the displacement of the third frame relative to the first frame increases by less than a factor of two when an external force applied to the compliant attachment increases by a factor of two.

13. The orthopedic fixator of claim 12, further comprising physical stops for limiting a displacement of the third frame relative to the first frame to a maximum distance, wherein the maximum distance is independent of the degree of compliance provided by the compliant attachment between the first and third frames.

14. The orthopedic fixator of claim 12, wherein the maximum displacement of the third frame relative to the first frame in a direction towards the second frame is different than the maximum displacement of the third frame relative to the first frame in the direction away from the second frame.

15. The orthopedic fixator of claim 12, wherein one of said first frame and said third frame further comprises angular openings and the other of said first frame and said third frame comprises radial extensions that extend within the angular openings to prevent the first and third frames from rotating relative to each other.

16. The orthopedic fixator of claim 12, further comprising:
multiple adjustable compliant attachments of the first frame to the third frame, the compliant attachments being independently adjustable to create a remote axis of rotation for the third frame.

17. The orthopedic fixator of claim 16, wherein the first and third frames are concentric.

18. The orthopedic fixator of claim 16, further comprising stops for limiting the displacement of the third frame relative to the first frame to a maximum distance, wherein the maximum distance is independent of the degree of compliance provided by the compliant attachment between the first and third frames.

19. The orthopedic fixator of claim 16, wherein the compliant attachments provide a nonlinear force-displacement response whereby the displacement of the third frame relative to the first frame increases by less than a factor of two when an external force applied to the compliant attachments increases by a factor of two.

20. The orthopedic fixator of claim 18, wherein the maximum displacement of the third frame relative to the first frame in a direction towards the second frame is different than the maximum displacement of the third frame relative to the first frame in the direction away from the second frame.

* * * * *